United States Patent
Kimura et al.

[11] Patent Number: 5,947,727
[45] Date of Patent: Sep. 7, 1999

[54] DENTAL TREATMENT APPARATUS

[75] Inventors: Shusuke Kimura; Shigeru Nakamura, both of Yono; Tatsuo Okazaki, Kami-Fukuoka, all of Japan

[73] Assignee: Kabushiki Kaisha Morita Tokyo Seisakusho, Yono, Japan

[21] Appl. No.: 09/220,350

[22] Filed: Dec. 24, 1998

[30] Foreign Application Priority Data

Dec. 27, 1997 [JP] Japan .................................. 9-367785

[51] Int. Cl.⁶ .................................................. A61G 17/02
[52] U.S. Cl. ............................................................ 433/80
[58] Field of Search .................................. 433/77, 78, 79, 433/80, 229; 422/23, 37

[56] References Cited

U.S. PATENT DOCUMENTS

| | | | |
|---|---|---|---|
| 4,215,476 | 8/1980 | Armstrong | 433/80 |
| 4,710,233 | 12/1987 | Hohmann et al. | 134/4 |
| 4,839,004 | 6/1989 | Castellini | 204/128 |
| 5,055,043 | 10/1991 | Weiss et al. | 433/80 |
| 5,295,829 | 3/1994 | Frey et al. | 433/80 |
| 5,360,338 | 11/1994 | Waggoner | 433/80 |
| 5,837,204 | 11/1998 | Prevost et al. | 433/80 |

*Primary Examiner*—John J. Wilson
*Assistant Examiner*—Patrick A. Hilsmier
*Attorney, Agent, or Firm*—Armstrong, Westerman, Hattori, McLeland & Naughton

[57] ABSTRACT

A dental treatment apparatus having a sterilized water producing unit placed in a water circuit of a dental chair unit. The sterilized water producing unit electrolyzes water mixed with sodium chloride and hydrochloric acid in a diaphragmless electrolytic cell to produce sterilized water having a residual free chlorine concentration adjusted in the range of from 1.0 ppm to 200 ppm and a pH adjusted in the range of from 3 to 7. The dental treatment apparatus further has a water circuit switching controller that alternately switches between raw water and feed water from the sterilized water producing unit.

2 Claims, 2 Drawing Sheets

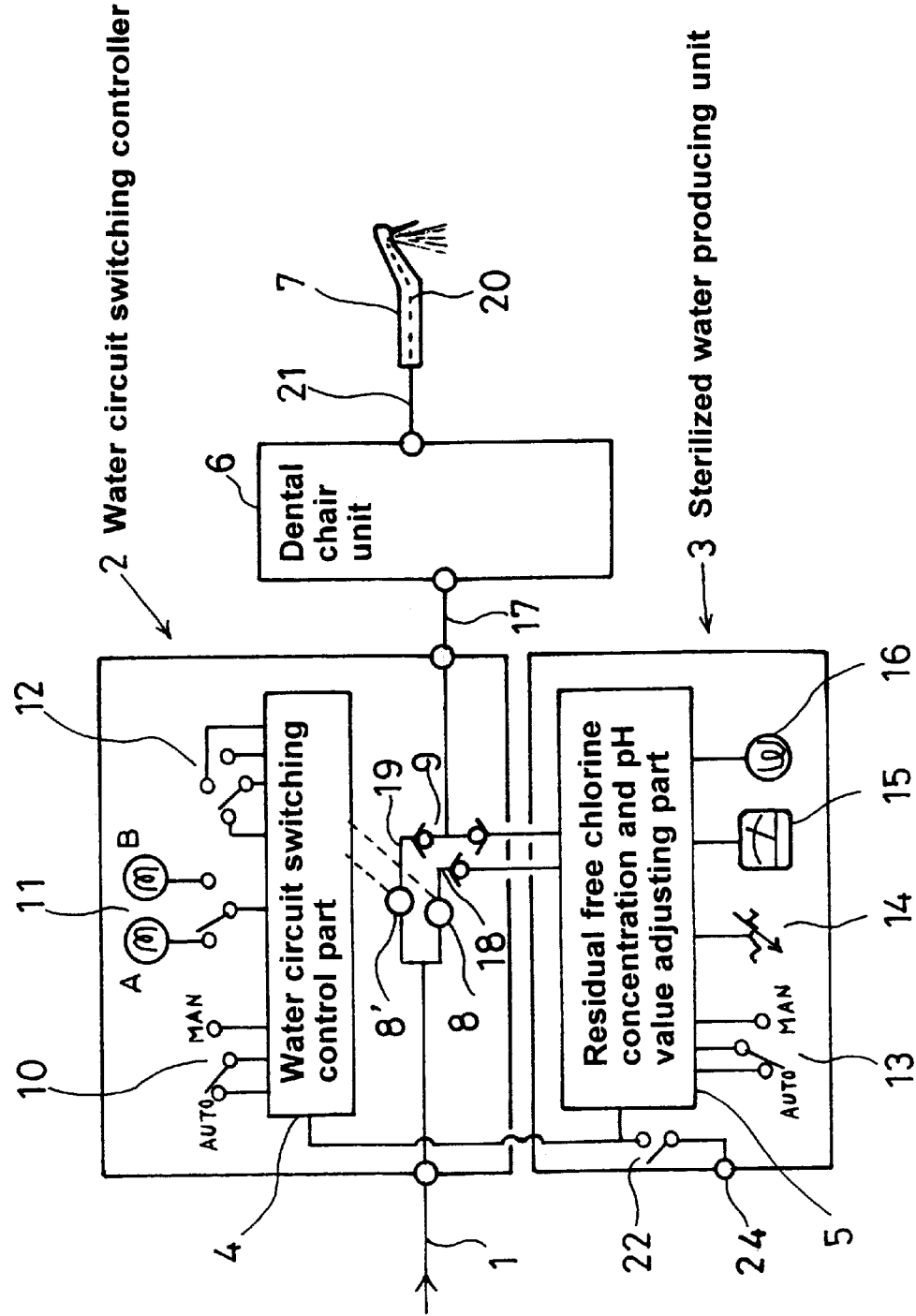

DENTAL TREATMENT APPARATUS

BACKGROUND OF THE INVENTION

The present invention relates to a sterilization apparatus used in a water circuit of a dental chair unit. More particularly, the present invention relates to a dental treatment apparatus having a sterilized water producing unit that adjusts the residual free chlorine concentration and pH value of water used for dental treatment, and a switching controller that switches between raw water and feed water from the sterilized water producing unit.

Conventionally, during dental treatment with a dental chair unit, the patient's oral cavity is cleaned with water jets from an instrument or by using a syringe or the like. At the time of suspending the treatment, suction is used to prevent water from dripping from the tip of the instrument. At this time, disease-causing bacteria in the patient's mouth may be sucked together with water, causing the water circuit of the treatment apparatus to be contaminated.

In a case where the dental chair unit is not used for a long period of time because of the dentist's day off, for example, bacteria may propagate in water left in the water circuit.

In a case where a filter is provided in a feed circuit of the water circuit, bacteria may propagate in the filter with passage of time.

For the reasons stated above, there have heretofore been cases where contaminated water is used in a patient's mouth, and the patient is infected with disease-causing bacteria.

On the other hand, there are cases where strong acid water having a pH of 3 or below is used for sterilization. However, this technique suffers from the problem that the strong acid water remaining the water circuit oxidizes metals used in the water circuit, causing them to be rusted.

SUMMARY OF THE INVENTION

In view of the above-described problems with the prior art, an object of the present invention is to provide a dental treatment apparatus whereby sterilized water is used for patients at all times and metals in the water circuit are prevented from rusting.

To attain the above-described object, the present invention provides a dental treatment apparatus having a sterilized water producing unit placed n a water circuit of a dental chair unit. The sterilized water producing unit electrolyzes water mixed with sodium chloride and hydrochloric acid in a diaphragmless electrolytic cell to produce sterilized water having a residual free chlorine concentration adjusted in the range of from 1.0 ppm to 200 ppm and a pH adjusted in the range of from 3 to 7.

Preferably, the dental treatment apparatus further has a water circuit switching controller that alternately switches between raw water and feed water from the sterilized water producing unit.

According to the present invention, the water circuit switching controller and the sterilized water producing unit are connected together to supply sterilized water to an instrument through the dental chair unit.

Still other objects and advantages of the invention will in part be obvious and will in part be apparent from the specification.

The invention accordingly comprises the features of construction, combinations of elements, and arrangement of parts which will be exemplified in the construction hereinafter set forth, and the scope of the invention will be indicated in the claims.

BRIEF DESCRIPTION OF THE DRAWINGS

FIG. 2 is a block diagram of the dental treatment apparatus.

DESCRIPTION OF THE PREFERRED EMBODIMENTS

The structure and operation of one embodiment of the dental treatment apparatus according to the present invention will be described below with reference to the accompanying drawings.

Figure 1:
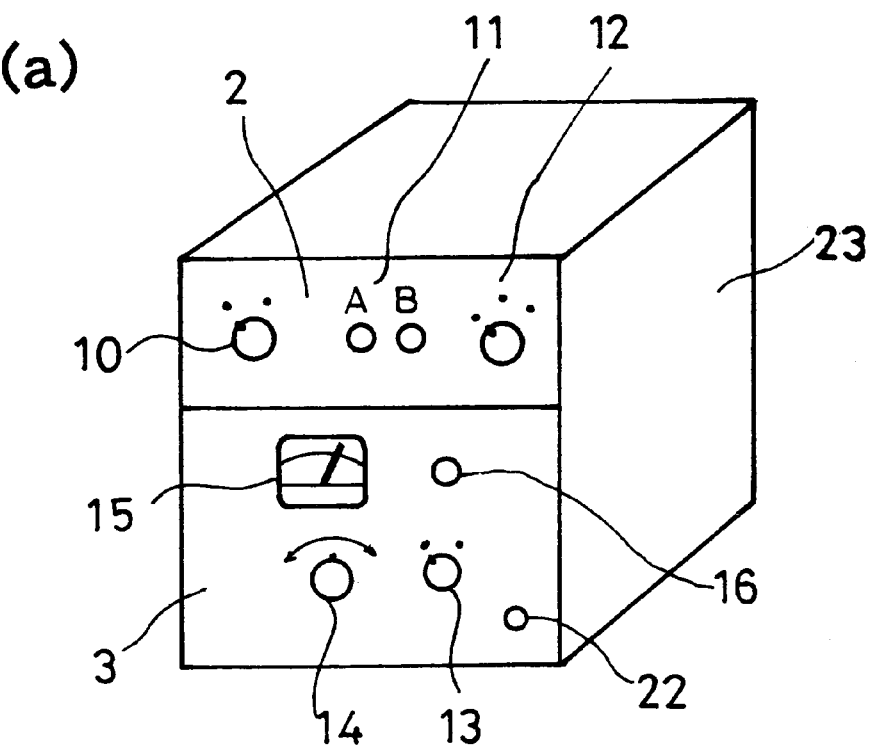
FIG. 1 is a perspective view showing the external appearance of a water circuit switching controller and sterilized water producing unit of a dental treatment apparatus according to the present invention.
Figure 1:
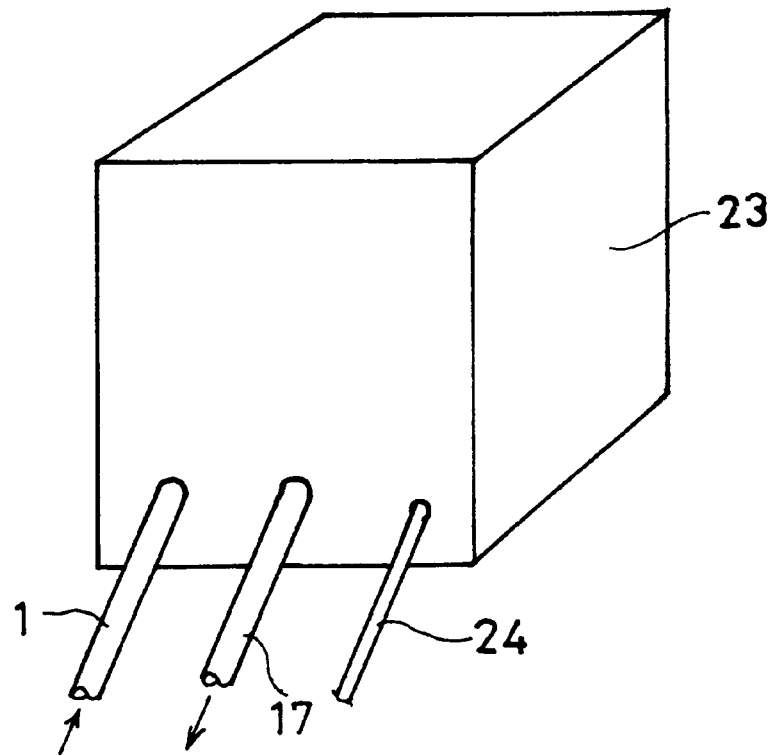

FIG. 1 is a perspective view showing the external appearance of a water circuit switching controller and sterilized water producing unit of the dental treatment apparatus according to the embodiment of the present invention.

Part (a) of FIG. 1 is a front perspective view showing the water circuit switching controller and the sterilized water producing unit. Part (b) of FIG. 1 is a rear perspective view of the arrangement shown in part (a) of FIG. 1. In FIG. 1: reference numeral 1 denotes a raw water supply hose; 2 a water circuit switching controller; 3 a sterilized water producing unit; 10 a water circuit auto-manual selection switch; 11 a water circuit indicating lamp; 12 a water introduction time setting device; 13 a residual free chlorine concentration adjustment auto-manual selection switch; 14 a residual free chlorine concentration setting device; 15 a residual free chlorine concentration indicator; 16 a pH indicating lamp; 17 a unit feed water hose; 23 an enclosure; and 24 a power supply cord.

As shown in part (a) of FIG. 1, the upper part of the front panel of the enclosure 23 is provided with the control switches (the water circuit auto-manual selection switch 10 and the water introduction time setting device 12) of the water circuit switching controller 2 and the water circuit indicating lamp 11. The lower part of the front panel is provided with the control switches (the residual free chlorine concentration adjustment auto-manual selection switch 13 and the residual free chlorine concentration setting device 14) of the sterilized water producing unit 3, together with the residual free chlorine concentration indicator 15 and the pH indicating lamp 16.

As shown in part (b) of FIG. 1, the rear side of the enclosure 23 is provided with the raw water supply hose 1, the unit feed water hose 17 and the power supply cord 24.

Feed water from the feed water hose 17 is, as shown in FIG. 2, supplied to an instrument 7 through a dental chair unit 6.

Next, the operation of the dental treatment apparatus according to the present invention will be described with reference to FIG. 2, which is a block diagram of the dental treatment apparatus.

In FIG. 2: reference numeral 5 denotes a residual free chlorine concentration and pH value adjusting part; 6 a dental chair unit; 7 an instrument; 8 and 8' solenoid valves; 9 check valves; 18 a water circuit A; 19 a water circuit B; 20 a water channel in the instrument; and 21 an instrument feed water hose.

First, the control flow and operation of the dental treatment apparatus according to the present invention will be described.

To introduce water from the raw water supply hose 1, a water circuit is selected by alternately switching on and off the solenoid valve 8 for the water circuit A or the solenoid valve 8' for the water circuit B under the control of a water circuit switching control part 4.

The water circuit selecting operation can be set in either an automatic mode or a manual mode by actuating the auto-manual selection switch 10. A selected water circuit is indicated by the water circuit indicating lamp 11.

The water introduction time for the water circuit can be set according to the frequency of use of the instrument 7, the length of time that the instrument 7 is used, etc. by actuating the water introduction time setting device 12.

When the water circuit B 19 is selected, raw water is supplied directly to the dental chair unit 6 through the unit feed water hose 17. When the water circuit A 18 is selected, raw water is supplied to the residual free chlorine concentration and pH value adjusting part 5, and sterilized water produced therein is supplied to the dental chair unit 6 through the unit feed water hose 17.

The check valves 9 are provided to prevent back flow when the water circuit A 18 and the water circuit B 19 are switched over from one to the other.

Raw water or sterilized water supplied to the dental chair unit 6 is sent to the instrument 7 through the instrument feed water hose 21, passed through the water channel 20 in the instrument 7 and jetted out from the tip of the instrument 7.

By virtue of the above-described control flow, after a patient has been treated with sterilized water, the inside of the water circuit is cleaned with raw water to prevent rusting of metals used in the water circuit.

Next, the sterilized water producing unit 3 will be described.

The sterilized water producing unit 3 is based on the sterilized water producing method (Japanese Patent No. 2619756, granted to the present applicant). In the sterilized water producing unit 3, water mixed with sodium chloride and water mixed with hydrochloric acid are mixed together and electrolyzed in a diaphragmless electrolytic cell, thereby continuously producing sterilized water having a residual free chlorine concentration adjusted in the range of from 1.0 ppm to 200 ppm and a pH value adjusted in the range of from 3 to 7, in which the abundance ratio of hypochlorous acid is high. Hypochlorous acid has a great sterilizing effect.

It should be noted that the abundance ratio of hypochlorous acid varies with the pH, and the residual free chlorine concentration and pH of electrolyzed water vary with the amount of water to be electrolyzed and also vary with the electrolytic current. However, in the sterilized water producing unit 3, there is no diaphragm used to separate the anode and cathode spaces. Therefore, the overall pH in the electrolytic cell leans toward the alkali pH. Consequently, the pH value can be readily adjusted by varying the amount of hydrochloric acid added to water.

According to the present invention, even if the sterilized water has a residual free chlorine concentration lower than that of an ordinary aqueous sodium hypochlorite solution for sterilization, which is not electrolyzed, it is possible to exhibit a sterilizing effect equal to that of the aqueous sodium hypochlorite solution.

In addition, because hydrochloric acid is added to water, there is no deposition of calcium on the cathode side in the electrolytic cell. Accordingly, the electrodes do not need maintenance, and there is no useless drainage of water.

Thus, sterilized water can be produced by a simple operation.

When the water circuit A 18 is selected to introduce raw water into the sterilized water producing unit 3, first, either an automatic mode or a manual mode is set by actuating the auto-manual selection switch 13.

The residual free chlorine concentration is adjusted in the range of from 1.0 ppm to 200 ppm by using the residual free chlorine concentration setting device 14 and the residual free chlorine concentration indicator 15. The pH value is adjusted in the range of from 3 to 7 by varying the amount of hydrochloric acid added to water. The pH indicating lamp 16 lights up to indicate that the water is fit for use.

In the foregoing embodiment, the water circuit switching controller 2 and the sterilized water producing unit 3 are formed in an integral structure separate from the dental chair unit 6. In use, the water circuit switching controller 2 and the sterilized water producing unit 3 and connected to the dental chair unit 6 by the unit feed water hose 17. However, the water circuit switching controller 2 and the sterilized water producing unit 3 may be incorporated into the dental chair unit 6.

Thus, the present invention provides the following advantageous effects:

According to the present invention, a dental chair unit is provided with a sterilized water producing unit. Therefore, sterilized water is supplied to a patient and used for treatment. Accordingly, it is possible to prevent secondary infection through water for treatment.

In addition, the dental treatment apparatus has a water circuit switching controller that alternately switches between raw water and feed water from the sterilized water producing unit. Accordingly, the water circuit is cleaned with raw water after treatment. Thus, metals in the water circuit can be prevented from corrosion.

It should be noted that the present invention is not limited to the foregoing embodiment but can be modified in a variety of ways.

What we claim is:

1. A dental treatment apparatus comprising:

a dental chair unit having a water circuit; and a sterilized water producing unit placed in said water circuit, said sterilized water producing unit electrolyzing water mixed with sodium chloride and hydrochloric acid in a diaphragmless electrolytic cell to produce sterilized water having a residual free chlorine concentration adjusted in a range of from 1.0 ppm to 200 ppm and a pH adjusted in a range of from 3 to 7.

2. A dental treatment apparatus according to claim 1, further comprising a water circuit switching controller that alternately switches between raw water and feed water from said sterilized water producing unit.

* * * * *